(12) United States Patent
Sanuki et al.

(10) Patent No.: US 10,813,765 B2
(45) Date of Patent: Oct. 27, 2020

(54) VOICE DISORDER TREATMENT TOOL AND VOICE DISORDER TREATMENT SET

(71) Applicants: NOBELPHARMA CO., LTD., Tokyo (JP); National University Corporation Kumamoto University, Kumamoto-shi, Kumamoto (JP); Wakayoshi Seisakusho Co., Ltd., Sabae-shi, Fukui (JP)

(72) Inventors: Tetsuji Sanuki, Kumamoto (JP); Shuji Wakayoshi, Fukui (JP); Tsukasa Harada, Fukui (JP); Seiichi Masuda, Fukui (JP); Hiroyuki Nishihata, Fukui (JP); Kazuhiro Kinoshita, Tokyo (JP); Takako Aburada, Tokyo (JP)

(73) Assignees: NOBELPHARMA CO., LTD., Tokyo (JP); NATIONAL UNIVERSITY CORPORATION KUMAMOTO UNIVERSITY, Kumamoto (JP); WAKAYOSHI SEISAKUSHO CO., LTD., Fukui (JP)

( * ) Notice: Subject to any disclaimer, the term of this patent is extended or adjusted under 35 U.S.C. 154(b) by 0 days.

(21) Appl. No.: 15/751,361
(22) PCT Filed: Aug. 9, 2016
(86) PCT No.: PCT/JP2016/073481
§ 371 (c)(1),
(2) Date: Feb. 8, 2018
(87) PCT Pub. No.: WO2017/026493
PCT Pub. Date: Feb. 16, 2017

(65) Prior Publication Data
US 2018/0228611 A1 Aug. 16, 2018

(30) Foreign Application Priority Data
Aug. 10, 2015 (JP) .................................. 2015-158456

(51) Int. Cl.
A61F 2/30 (2006.01)
A61F 2/46 (2006.01)
A61F 2/20 (2006.01)

(52) U.S. Cl.
CPC ............ *A61F 2/30756* (2013.01); *A61F 2/20* (2013.01); *A61F 2/30749* (2013.01);
(Continued)

(58) Field of Classification Search
CPC ................ A61F 2/20; A61F 2/30; A61F 2/46
(Continued)

(56) References Cited

U.S. PATENT DOCUMENTS

| 4,130,905 A * | 12/1978 | Mercandino ............... A61F 2/18 623/10 |
| 5,306,298 A | 4/1994 | Godley, III et al. |
| 5,549,673 A * | 8/1996 | Beale ...................... A61B 17/24 128/898 |
| 5,855,607 A * | 1/1999 | Friedrich .................. A61F 2/20 623/9 |

(Continued)

FOREIGN PATENT DOCUMENTS

JP 2005-000330 1/2005

OTHER PUBLICATIONS

Sanuki, et al., "Surgical treatment for adductor spasmodic dysphonia", Jibi to Rinsho, vol. 51, No. 5, 2005, pp. 381-386, see p. 386 for English Abstract.

*Primary Examiner* — Suzette J Gherbi
(74) *Attorney, Agent, or Firm* — Hamre, Schumann, Mueller & Larson, P.C.

(57) ABSTRACT

[Problem] The present invention provides a voice disorder treatment tool in which a clamping section thereof does not break easily. [Solution] The present invention includes a plurality of clamping sections 1, 1 that are provided with a front surface piece 1b disposed on a front surface 11a of incised thyroid cartilage 11 and a rear surface piece 1c disposed on a rear surface of the thyroid cartilage 11, and fit to cut ends 12 of the incised thyroid cartilage 11 that are (Continued)

facing each other, and a bridging section 2 that connects the plurality of clamping sections 1, 1. The front surface piece 1b includes a bending region 15 deformable about a virtual line K extending in a width direction of this front surface piece 1b, and the bending region 15 has a reinforcing structure S.

9 Claims, 6 Drawing Sheets

(52) U.S. Cl.
CPC .... *A61F 2/4618* (2013.01); *A61F 2220/0008* (2013.01); *A61F 2250/0029* (2013.01); *A61F 2250/0036* (2013.01)

(58) Field of Classification Search
USPC .......................................... 623/9, 14.11, 11.11
See application file for complete search history.

(56) References Cited

U.S. PATENT DOCUMENTS

| | | | |
|---|---|---|---|
| 6,159,243 A * | 12/2000 | Schouwenburg | A61B 17/24 606/108 |
| 7,090,697 B2 * | 8/2006 | Isshiki | A61F 2/20 623/11.11 |
| 9,220,507 B1 * | 12/2015 | Patel | A61B 17/1227 |
| 10,335,269 B2 * | 7/2019 | Fahl | A61F 2/20 |
| 2004/0254642 A1 * | 12/2004 | Isshiki | A61F 2/20 623/11.11 |
| 2010/0023125 A1 * | 1/2010 | Debry | A61F 2/20 623/14.11 |
| 2016/0183958 A1 * | 6/2016 | McCulloch | A61B 17/0401 623/14.11 |
| 2016/0354199 A1 * | 12/2016 | Fahl | A61F 2/20 |
| 2017/0231754 A1 * | 8/2017 | Ho | A61F 2/20 623/9 |
| 2018/0228611 A1 * | 8/2018 | Sanuki | A61F 2/30749 |

* cited by examiner

VOICE DISORDER TREATMENT TOOL AND VOICE DISORDER TREATMENT SET

FIELD OF THE INVENTION

The present invention relates to a voice disorder treatment tool and a voice disorder treatment set.

BACKGROUND OF THE INVENTION

To improve spasmodic dysphonia, a condition in which vocal cords fail to vibrate due to excessive glottic closure or the like, there has been proposed the voice disorder treatment tool disclosed in Patent Document 1 below.

The voice disorder treatment tool disclosed in Patent Document 1 includes two clamping sections made from titanium that clamp cut ends on both sides of incised thyroid cartilage, and a bridging section made from titanium that bridges the two clamping sections and maintains the incision space of the incised thyroid cartilage. The clamping sections each include a front surface piece disposed on a front surface side of the incised thyroid cartilage, and a rear surface piece disposed on a rear surface side of the thyroid cartilage.

To use this treatment tool, first the front surface piece of each clamping section is bent at a position near the bridging section. As a result, the shapes of the front surface pieces are made to extend along the shapes of the sections of the thyroid cartilage where the treatment tool is to be set. Then, an incision is made in the center of the thyroid cartilage, the cut ends of the thyroid cartilage are spread open by forceps, the clamping sections are fit to the cut ends spread apart and facing each other, and the forceps are removed. Then, the spread cut ends elastically return in a closing direction, thereby fixing the treatment tool securely between the cut ends.

Further, a suture thread is passed through circular holes formed in positions near the bridging section of the front surface pieces for the purpose of gripping the treatment tool or the like, thereby sewing the treatment tool and the thyroid cartilage together. As a result, displacement of the set treatment tool at the cut ends is more reliably prevented. With the above, the treatment tool can be reliably secured between the spread thyroid cartilage.

PRIOR ART DOCUMENTS

Patent Documents

Patent Document 1: JP 2005-000330 A

SUMMARY OF THE INVENTION

Problem to be Solved by Invention

The voice disorder treatment tool fixed to the thyroid cartilage vibrates in accordance with the vibration of the vocal cords, which mainly occurs during speech and deglutition. With this vibration, stress is understood to concentrate in the areas surrounding the holes formed in the regions where the front surface pieces are bent. Even though the clamping sections of the voice disorder treatment tool are covered and fixed by scar tissue, the clamping sections may break at locations where the distance between both side end edges of the clamping sections and the opening end edges of the holes are smallest.

Thus, it is an object of the present invention to provide a voice disorder treatment tool in which a clamping section thereof does not break easily.

Means for Solving the Problem

[1] A voice disorder treatment tool according to the embodiment of the present invention includes a plurality of clamping sections that are provided with a front surface piece disposed on a front surface of incised thyroid cartilage and a rear surface piece disposed on a rear surface of the thyroid cartilage, and fit to cut ends of the incised thyroid cartilage that are facing each other, and a bridging section that connects the plurality of clamping sections. The front surface piece includes a bending region deformable about a virtual line extending in a width direction of the front surface piece, and the bending region has a reinforcing structure.

An embodiment of the present invention, with the reinforcing structure of the bending region, makes it possible to alleviate stress applied to the bending region.

[2] The bending region of the voice disorder treatment tool according to the embodiment of the present invention may include a hole that allows a suture thread to be inserted therethrough, and the reinforcing structure may be configured by forming the hole into a long hole extending in a direction that intersects in the width direction.

An embodiment of the present invention makes it possible to disperse the stress potentially applied to a plate section surrounding the hole in a longitudinal direction of the front surface piece.

[3] The bending region of the voice disorder treatment tool according to the embodiment of the present invention includes a hole that allows a suture thread to be inserted therethrough, and the reinforcing structure is formed by curving a side end edge of the front surface piece in accordance with an opening end edge of the hole.

An embodiment of the present invention maintains a plate width on both sides of the hole formed in the bending region, making it possible to disperse the stress applied to the bending region.

[4] The reinforcing structure of the voice disorder treatment tool according to the embodiment of the present invention is configured by forming the hole further on a tip end side of the front surface piece than the virtual line.

An embodiment of the present invention makes it possible to shift the periphery of the hole susceptible to breakage in the front surface piece from the virtual line.

[5] The reinforcing structure of the voice disorder treatment tool according to the embodiment of the present invention is formed by making a thickness of the bending region, in part or in whole, greater than a thickness of other sections.

An embodiment of the present invention makes it possible to increase a rigidity of the bending region.

[6] The reinforcing structure of the voice disorder treatment tool according to the embodiment of the present invention includes a notch that allows hooking of a suture thread, the notch being provided on each side end edge of both ends of the front surface piece in the width direction.

An embodiment of the present invention makes it possible to sufficiently maintain a plate width of the bending region.

[7] The reinforcing structure of the voice disorder treatment tool according to the embodiment of the present invention includes a recessed line that allows hooking of a suture thread, the recessed line being provided on a front surface of the front surface piece.

An embodiment of the present invention makes it possible to sufficiently maintain the plate width of the bending region.

[8] The front surface piece of the voice disorder treatment tool according to the embodiment of the present invention may include a handle section that allows gripping by a tool.

An embodiment of the present invention makes it possible for an operator to reliably hold the voice disorder treatment tool.

[9] The front surface piece of at least one of the clamping sections according to the embodiment of the present invention may branch in two directions.

With the front surface piece of at least one of the clamping sections according to the embodiment of the present invention formed so as to branch in two directions, the front surface piece is readily fit to the shape of the thyroid cartilage.

[10] The front surface piece of the voice disorder treatment tool according to the embodiment of the present invention may be formed so as to curve along the incised thyroid cartilage in the bending region.

An embodiment of the present invention makes it possible to make the bend of the front surface piece for achieving an optimal bending state in the bending region the bare minimum.

[11] A voice disorder treatment set according to the embodiment of the present invention includes a plurality of any one of the voice disorder treatment tools described above, the voice disorder treatment tools being arrangeable above and below the incised thyroid cartilage.

The voice disorder treatment set according to the embodiment of the present invention exhibits any one of the actions or functions described above.

Effect of the Invention

The voice disorder treatment tool of the present invention exhibits such effects that the clamping sections are less susceptible to breakage in the bending region.

DESCRIPTION OF THE EMBODIMENTS

Embodiments of a voice disorder treatment tool of the present invention are described below with reference to accompanying drawings.

First, a first embodiment of the present invention will be described.

Figure 1:
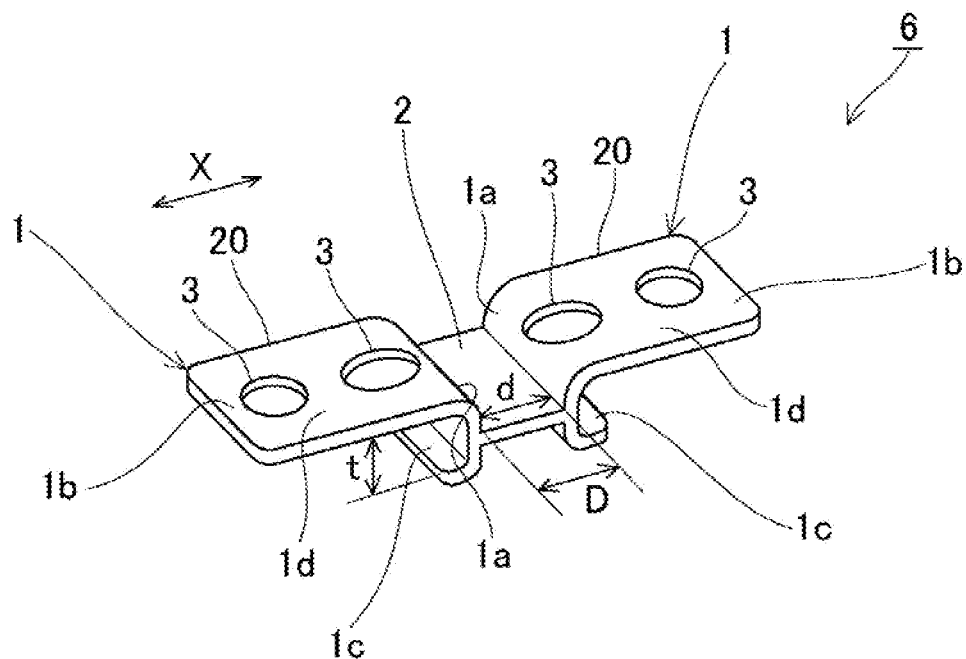
FIG. 1: A perspective view of a voice disorder treatment tool of the first embodiment of the present invention.
Figure 2:
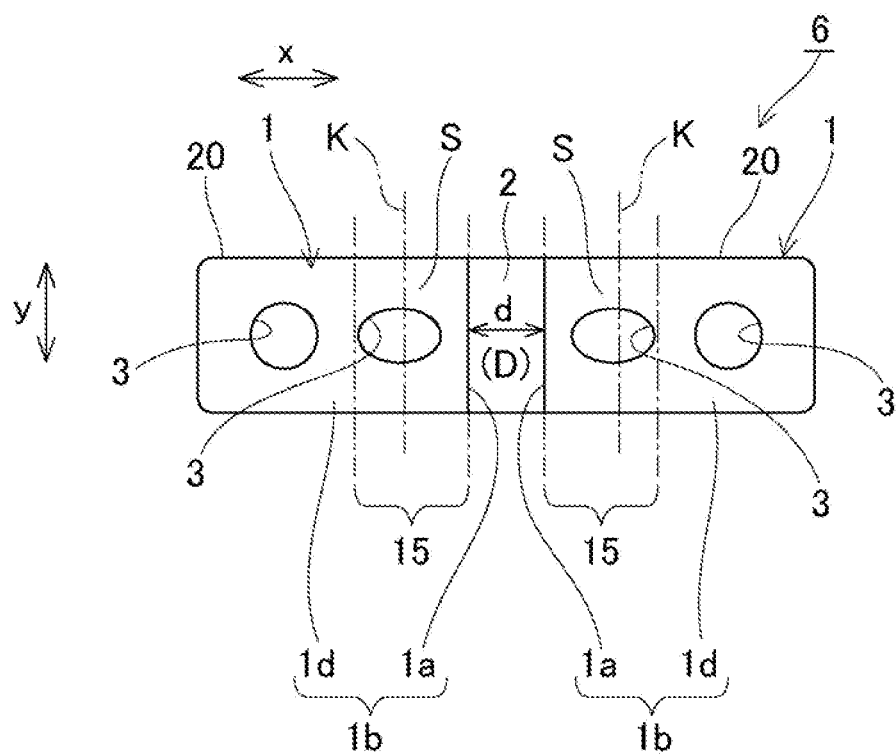
FIG. 2: A planar view of the voice disorder treatment tool of the first embodiment of the present invention.

As illustrated in FIGS. 1 and 2, a voice disorder treatment tool (hereinafter "treatment tool") 6 of the first embodiment of the present invention includes a plurality (one set of one pair in the present embodiment) of clamping sections 1, 1 that are provided with a front surface piece 1b and a rear surface piece 1c and fit to cut ends 12, 12 of thyroid cartilage 11 (illustrated in FIG. 3) that was incised, the cut ends 12, 12 facing each other, and a bridging section 2 that connects the plurality of clamping sections 1, 1.

Figure 3:
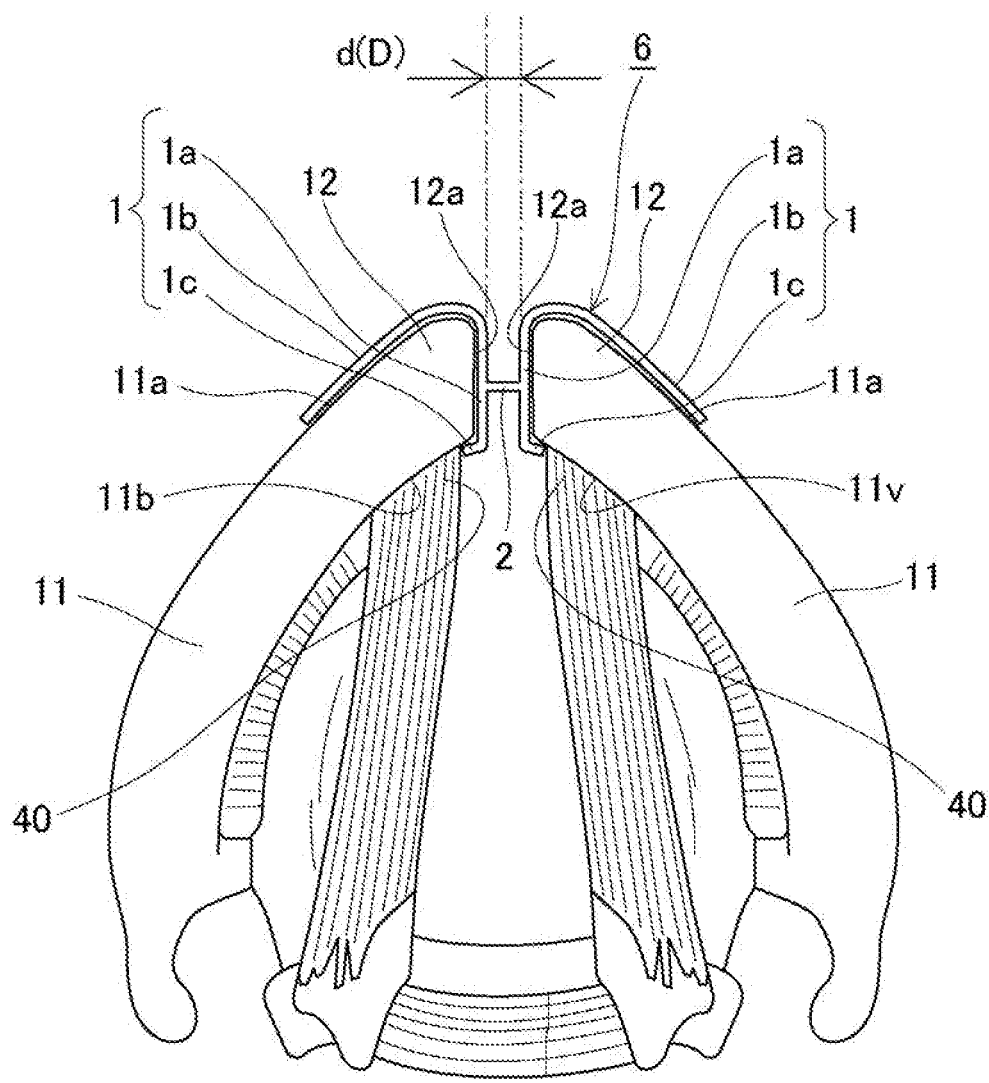
FIG. 3: A diagram illustrating an installed state of the voice disorder treatment tool illustrated as the first embodiment of the present invention.

The front surface piece 1b is formed into a substantially strip-like plate shape in a planar view. An end surface section 1a that is bent and made to contact a cut end surface 12a of the thyroid cartilage 11 illustrated in FIG. 3 is formed on a base end side of the front surface piece 1b in a longitudinal direction x. A front surface contacting section 1d that is made to contact a front surface 11a of the thyroid cartilage 11 is formed on a tip end side of the end surface section 1a of the front surface piece 1b.

A plurality (two in the present embodiment) of holes 3 are formed in the front surface piece 1b, at an interval in the longitudinal direction x.

These holes 3, 3 allow a suture thread (not illustrated; hereinafter the same) to be inserted therethrough, and are formed to a size from 1.0 to 2.0 mm, allowing a suture needle to be inserted therethrough.

The front surface piece 1b, as illustrated in FIG. 2, includes a bending region 15 deformable about a virtual line K that extends in a width direction y of the front surface piece 1b. The set position of the virtual line K is determined in accordance with the shape of the cut end 12 (refer to FIG. 3) of the individual patient to ensure close contact can be made with the cut end 12 of the patient. The range in which this virtual line K can be set is equivalent to the bending region 15. Specifically, the bending region 15 is generally set to a range of from 1.0 to 6.0 mm from a base end of the front surface contacting section 1d.

In the present embodiment, the bending region 15 includes a reinforcing structure S configured by forming the hole 3 into the long hole 3 that extends in a direction that intersects the width direction y, that is, extends in the substantially longitudinal direction x.

Figure 4:
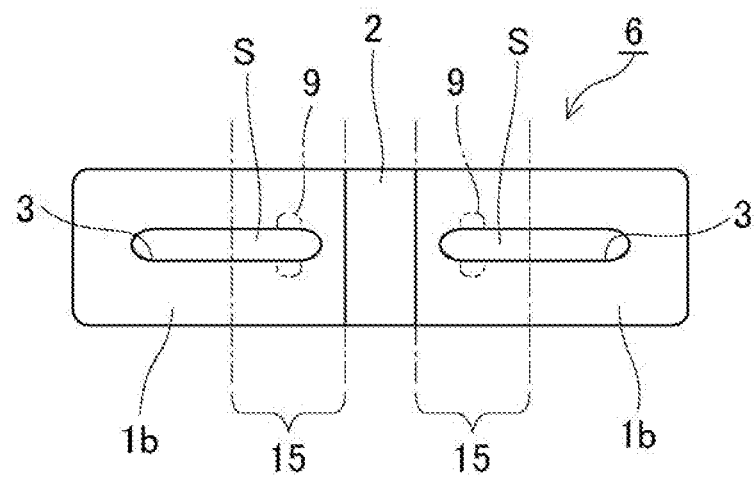
FIG. 4: A planar view of a modification of the voice disorder treatment tool illustrated as the first embodiment of the present invention.

Specifically, the hole 3 is formed into an elliptical shape. Note that the long hole 3 is not limited to an elliptical shape and, as long as the shape includes a section formed as parallel as possible with a side end edge 20 of the front surface piece 1b, in other words, as long as the shape is formed longer in the longitudinal direction x than when the hole 3 is a circle, the shape may be substantially rectangular or, as illustrated in FIG. 4, a shape having long sides that are mutually parallel and short sides that are semicircular, or the like. Note that, when the hole 3 is formed as illustrated in FIG. 4, a depression section 9 (illustrated by the chain double-dashed line in FIG. 4) that allows hooking of a suture thread may be formed.

As illustrated in FIGS. 1 and 3, the rear surface piece 1c is a section that bends from the end surface section 1a of the front surface piece 1b toward a rear surface 11b side of the thyroid cartilage 11 illustrated in FIG. 3.

The front surface piece 1b and the rear surface piece 1c are integrally formed to constitute the clamping section 1, and the clamping section 1 is formed into a substantially J shape (reverse J shape) as a whole.

In the clamping section 1, a length of the front surface piece 1b is a necessary and sufficient length for clamping the thyroid cartilage 11, is preferably a length that can extend along the form of the thyroid cartilage, and specifically is preferably about from 8 to 12 mm. Further, the rear surface piece 1c is preferably set to a length that allows contact from an end edge of the cut end 12 of the thyroid cartilage 11 to an end edge of soft tissue 40 below the thyroid cartilage 11, and specifically is preferably about from 1.5 to 5.5 mm.

The clamping sections 1, as illustrated in FIGS. 1 to 3, are provided symmetrically so that the clamping sections 1 can be fitted to the mutually facing cut ends 12, 12 of the thyroid cartilage 11, disposing the front surface piece 1b on the cut end surface 12a and the front surface 11a side of the thyroid cartilage 11 and the rear surface piece 1c on the rear surface 1b side of the thyroid cartilage 11, and are linked by the bridging section 2.

The bridging section 2 is a section that links the clamping sections 1, and links the clamping sections 1 in an intermediate section in the extending direction of the end surface section 1a. A length d of the bridging section 2, that is a space D between both of the clamping sections 1, 1, is equivalent to a distance between the cut ends 12, 12 of the spread thyroid cartilage 11 and, while differing in accordance with the symptoms, body type, and voice state of the patient with a voice disorder, is generally set within a range of from 2 to 6 mm.

The clamping sections 1 and the bridging section 2 are both made from titanium.

The titanium metal applicable in the present invention is not limited to titanium as a pure metal, and includes titanium alloys used in artificial bones, artificial joints, and dental implants as a biomedical metal material. Specifically, Ti-6Al-4V which does not contain Ni, an element identified as a cause of cancer and allergies, and known as a titanium alloy superior in biocompatibility or the like may be used. To prevent wear as well as elution, the titanium or titanium alloy may be injected with N or C ions to modify the surface, or subjected to anodic oxidation or the like to give the material a preferred color.

A space (width dimension of the end surface section 1a) t between the front surface contacting section 1d and rear surface piece 1c illustrated in FIG. 1 is preferably slightly greater than a thickness dimension of the thyroid cartilage 11, and specifically is preferably about from 2 to 4 mm. When the space t is less than the thickness dimension of the thyroid cartilage 11 illustrated in FIG. 3, the thyroid cartilage 11 is squeezed, and the clamping sections 1 continually apply pressure on the thyroid cartilage 11 for a long period of time, resulting in the possibility of erosion and damage to the thyroid cartilage 11. On the other hand, when the space t between the front surface contacting section 1d and the rear surface piece 1c is excessively large compared to the thickness dimension of the thyroid cartilage 11, the thyroid cartilage 11 becomes substantially difficult to clamp, making the clamping sections 1 relatively more susceptible to shifting (sliding) with respect to the thyroid cartilage 11.

Next, the method of using the treatment tool 6 according to the embodiment of the present invention will be described with reference to FIGS. 1 to 3.

First, an incision is made in the center section of the thyroid cartilage 11, and the space between the cut ends 12, 12 for voice improvement is determined. Once the space for spreading is determined, the treatment tool 6 having a length d of the bridging section 2 in accordance with the space is selected, and the front surface pieces 1b in the bending regions 15 of the front surface pieces 1b are deformed as necessary so that the front surface contacting section 1d comes into contact with the front surface 11a of the thyroid cartilage 11. Then, the front surface pieces 1b are made to contact the front surfaces 11a and cut end surfaces 12a of the thyroid cartilage 11, and the clamping sections 1 are fit to the cut ends 12 so that the rear surface pieces 1c come into contact with the rear surfaces 11b of the thyroid cartilage 11.

Tip ends of the rear surface pieces 1c are inserted between the thyroid cartilage 11 and the soft tissue 40 therebelow so that the treatment tool 6 is attached with only the thyroid cartilage 11 clamped by the clamping sections 1. In the treatment tool 6 of the present invention, the rear surface pieces 1c are formed by a thin sheet of titanium, and thus the tip end sections of the rear surface pieces 1c can be relatively easily inserted between the thyroid cartilage 11 and the soft tissue 40.

The space t between the front surface contacting section 1d and the rear surface piece 1c of the clamping section 1 is formed slightly larger than a thickness of the clamped cartilage and thus, to more strongly secure the treatment tool 6, preferably a thread is passed through the hole 3 near the end surface section 1a to suture and fix the clamping section 1 and the thyroid cartilage 11 together. Further, a thread is passed through the hole 3 on the tip end side in the longitudinal direction x and sutured to the thyroid cartilage 11 as necessary. Such suturing work can be performed with the clamping sections 1 of the treatment tool 6 set and temporarily placed on the cut ends 12 of the thyroid cartilage 11 and thus, compared to a conventional silicon block, can be performed with relative leeway.

While the treatment tool 6 according to the embodiment of the present invention can be attached at suitable positions of the cut ends 12 as long as the positions can maintain the incision of the thyroid cartilage 11, the treatment tool 6 may be attached to two locations of a downward section and an upward section of the thyroid cartilage 11.

In the treatment tool 6 thus installed on the thyroid cartilage 11 of the patient, the hole 3 formed in each of the bending regions 15 is formed as a long hole extending in the longitudinal direction x, making it possible to dissipate the stress potentially applied to the plate section surrounding the hole 3 by an elastic return force that acts in the direction in which the thyroid cartilage 11 closes and vibration during speech and deglutition, and thus prevent stress concentration.

This achieves the effect of making it possible to effectively prevent breakage of the front surface pieces 1b caused by the concentration of stress in the bending regions 15.

Figure 5:
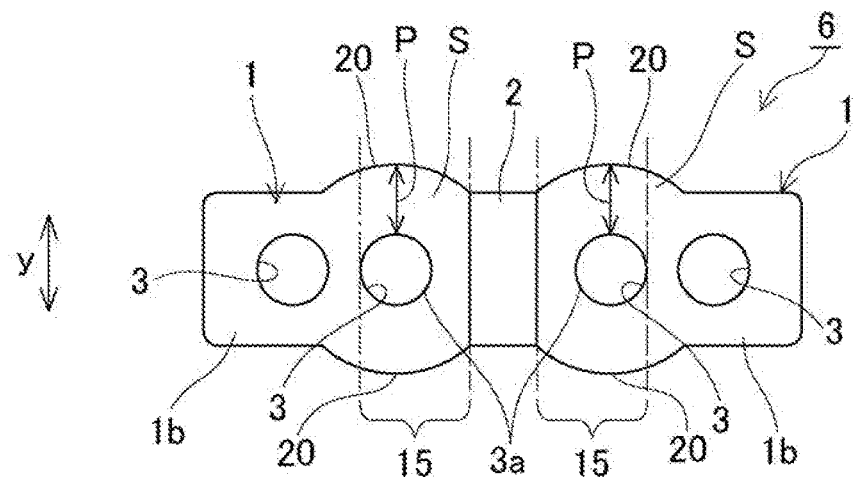
FIG. 5: A planar view of the voice disorder treatment tool illustrated as the second embodiment of the present invention.

Next, a second embodiment of the present invention will be described with reference to FIG. 5. In the present embodiment, the description focuses on the differences from the first embodiment, and thus the same components as those of the first embodiment are denoted using the same reference numerals, and descriptions thereof will be omitted.

In the treatment tool 6 of the second embodiment, the reinforcing structure S is configured by curving the side end edge 20 of the front surface piece 1*b* in accordance with the shape of an opening end edge 3*a* of the hole 3.

Specifically, the shape of the side end edge 20 of the front surface piece 1*b* extends substantially along the shape of the hole 3 formed in the bending region 15, and is thus formed to smoothly curve and protrude outward in the width direction y.

With the front surface piece 1*b* thus formed, a width P of the plate section surrounding the hole 3 formed in the bending region 15 is maintained. Accordingly, in the bending region 15, it is possible to dissipate the stress potentially applied to the plate section surrounding the hole 3 caused by the elastic return force that acts in the direction in which the thyroid cartilage 11 closes or vibration during speech and deglutition, and thus prevent stress concentration.

This achieves the effect of making it possible to effectively prevent breakage of the front surface pieces 1*b* caused by the concentration of stress in the bending regions 15.

Figure 6:
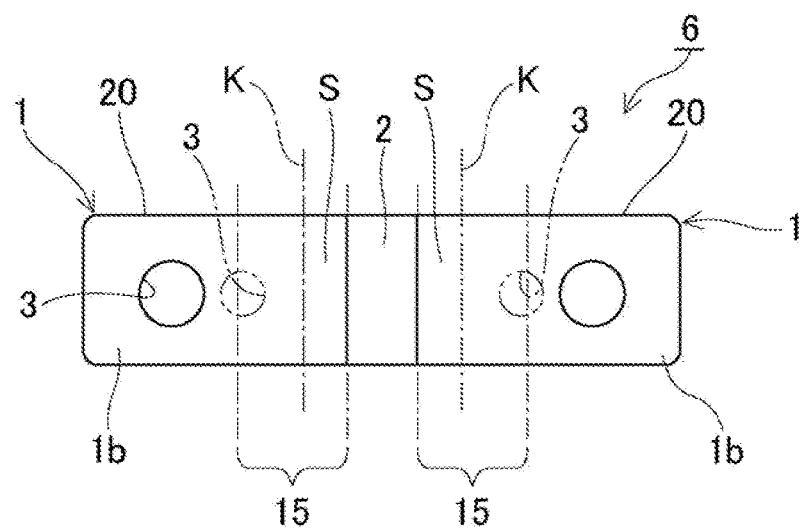
FIG. 6: A planar view of the voice disorder treatment tool illustrated as the third embodiment of the present invention.

Next, a third embodiment of the present invention will be described with reference to FIG. 6. In the present embodiment, the description focuses on the differences from the first embodiment, and thus the same components as those of the first embodiment are denoted using the same reference numerals, and descriptions thereof will be omitted.

In the treatment tool 6 of the third embodiment, the reinforcing structure S is configured by forming the hole 3 further on the tip end side of the front surface piece 1*b* than the virtual line K.

In the present embodiment, breakage of the front surface piece 1*b* is prevented by staggering the position most susceptible to breakage in the area surrounding the hole 3 formed in the bending region 15, that is, the area with the least distance between the hole 3 and the side end edge 20, and the set position of the virtual line K that is susceptible to stress.

Other examples of the present embodiment include a configuration in which the bending region 15 is formed without holes and the hole 3 is formed further on the tip end side of the front surface piece 1*b* than the bending region 15.

With this configuration, the effect of making it possible to effectively prevent breakage of the front surface pieces 1*b* caused by the concentration of stress in the bending regions 15 is achieved.

Figure 7:
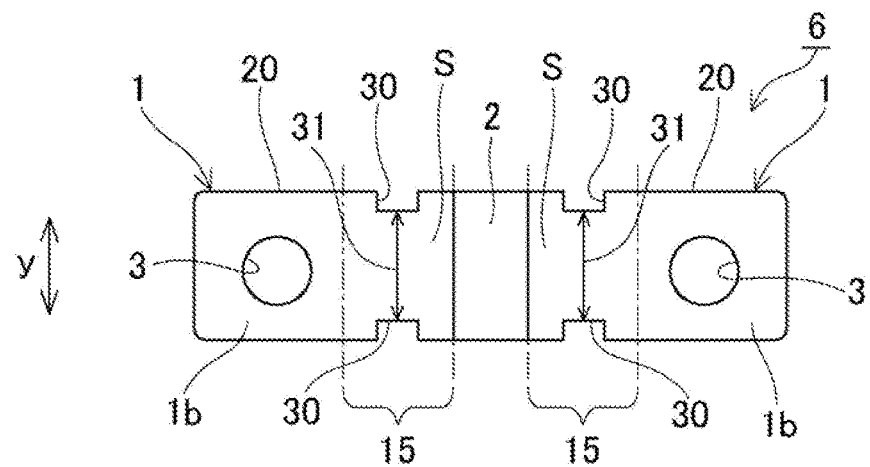
FIG. 7: A planar view of the voice disorder treatment tool illustrated as the fourth embodiment of the present invention.

Next, a fourth embodiment of the present invention will be described with reference to FIG. 7. In the present embodiment, the description focuses on the differences from the first embodiment, and thus the same components as those of the first embodiment are denoted using the same reference numerals, and descriptions thereof will be omitted.

In the treatment tool 6 of the fourth embodiment, the reinforcing structure S is configured by providing notches 30 to the side end edges 20 of both ends in the width direction y of the front surface piece 1*b*. This notch 30 allows hooking of the suture thread thereto.

Specifically, in the treatment tool 6 of the fourth embodiment, rather than forming the hole 3 that can cause the front surface piece 1*b* to break due to the stress that occurs by vibration during speech and deglutition or the elastic return force that acts in the direction in which the thyroid cartilage 11 closes in the bending region 15, notches 30, 30 that hook the suture thread are formed on the side end edges 20. The notch 30 may be any shape, but is preferably formed into a shape such as a rectangle or semicircle that is not susceptible to stress concentration.

Dimensions 31, 31 between the notches 30, 30 facing each other in the width direction y are formed within a range of from 2.0 to 4.0 mm.

The treatment tool 6 of the present embodiment has a width dimension of the front surface piece 1*b* that can withstand the stress caused by the vibration of the thyroid cartilage 11 or the elastic return force that acts in the direction in which the thyroid cartilage 11 closes, the width dimension is located between the notches 30,30 of the bending region 15, and this area is formed into a shape not susceptible to stress concentration and constitutes the reinforcing structure S. That causes the effect that may be able to effectively prevent breakage of the front surface pieces 1*b* while forming the hooking sections of the suture thread is achieved.

Figure 8:
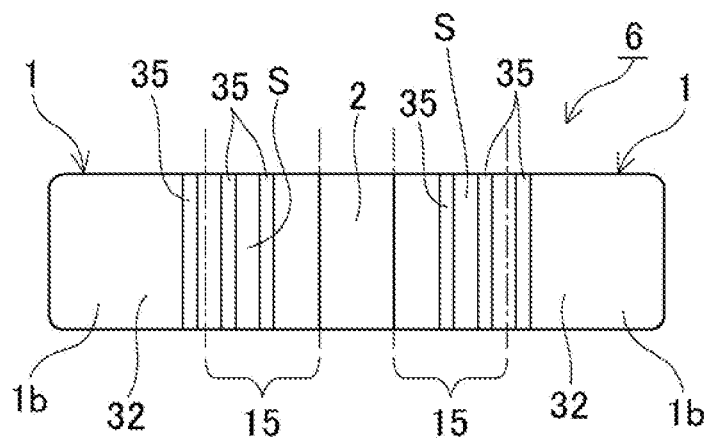
FIG. 8: A planar view of the voice disorder treatment tool illustrated as the fifth embodiment of the present invention.

Next, a fifth embodiment of the present invention will be described with reference to FIG. 8. In the present embodiment, the description focuses on the differences from the first embodiment, and thus the same components as those of the first embodiment are denoted using the same reference numerals, and descriptions thereof will be omitted.

In the treatment tool 6 of the fifth embodiment, the reinforcing structure S is configured by providing recessed lines 35, 35 to plate surfaces 32, 32 of the front surface piece 1*b*. The recessed lines 35 allow hooking of the suture thread thereto.

Specifically, in the treatment tool 6 of the fifth embodiment, rather than forming the hole 3 that potentially causes the front surface piece 1*b* to break due to the stress caused by vibration of the thyroid cartilage 11 or by the elastic return force that acts in the direction in which the thyroid cartilage 11 closes in the bending region 15, the recessed line 35 that hooks the suture thread is formed on at least one of the side surfaces 32 of the front surface piece 1*b*.

The recessed line 35 may have any cross-sectional shape as long as the shape is not susceptible to stress concentration, but is preferably formed into a shape having a rectangular cross section or the like that is not susceptible to stress concentration.

The treatment tool 6 has a width dimension of the front surface piece 1*b* that can withstand the stress caused by the vibration of the thyroid cartilage 11 or the elastic return force that acts in the direction in which the thyroid cartilage 11 closes. Further, the recessed line 35 is formed into a cross-sectional shape not susceptible to stress concentration. These constitute the reinforcing structure S. Thus, the effect of making it possible to effectively prevent breakage of the front surface pieces 1*b* while forming the hook sections of the suture thread is achieved.

Next, a sixth embodiment of the present invention will be described with reference to FIGS. 9 to 11. In the present embodiment, the description focuses on the differences from the first embodiment, and thus the same components as those of the first embodiment are denoted using the same reference numerals, and descriptions thereof will be omitted.

In the treatment tool 6 of the sixth embodiment, the reinforcing structure S is configured by making the thickness of the bending region 15 thicker in part or in whole than the thickness of other sections.

Figure 9:
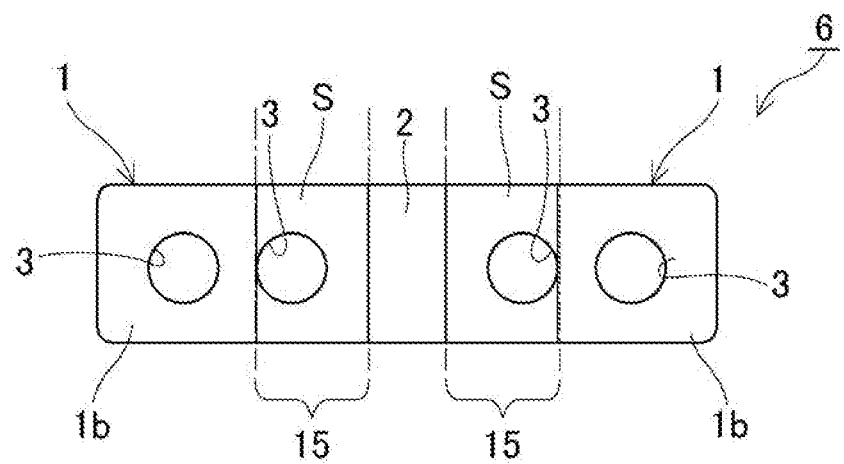
FIG. 9: A planar view of the voice disorder treatment tool illustrated as the sixth embodiment of the present invention.

Specifically, examples include forming the entire bending region 15 to a thickness greater than that of all other sections, as illustrated in FIG. 9.

Figure 10:
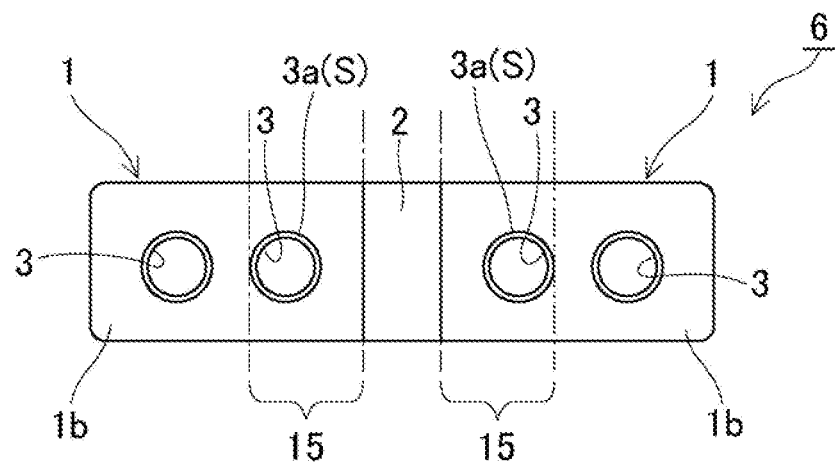
FIG. 10: A planar view of the voice disorder treatment tool illustrated as the sixth embodiment of the present invention.
Figure 11:
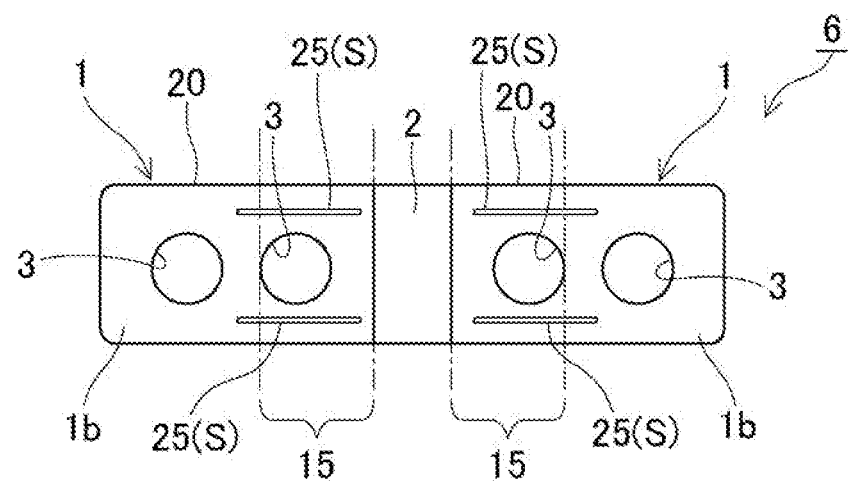
FIG. 11: A planar view of the voice disorder treatment tool illustrated as the sixth embodiment of the present invention.

Other examples include forming the opening end edge 3*a* of the hole 3 formed in the bending region 15 to a thickness greater than that of all other section as illustrated in FIG. 10, and configuring the reinforcing structure S by forming protruding lines 25, 25 parallel to the side end edge 20 of the front surface piece 1*b* across the range in which stress is readily applied to the hole 3 formed in the bending region 15 as illustrated in FIG. 11.

The reinforcing structure S of the present embodiment exhibits the effect of making it possible to increase the rigidity of locations susceptible to stress and preventing a section of the front surface piece 1*b* from breaking.

Figure 12:
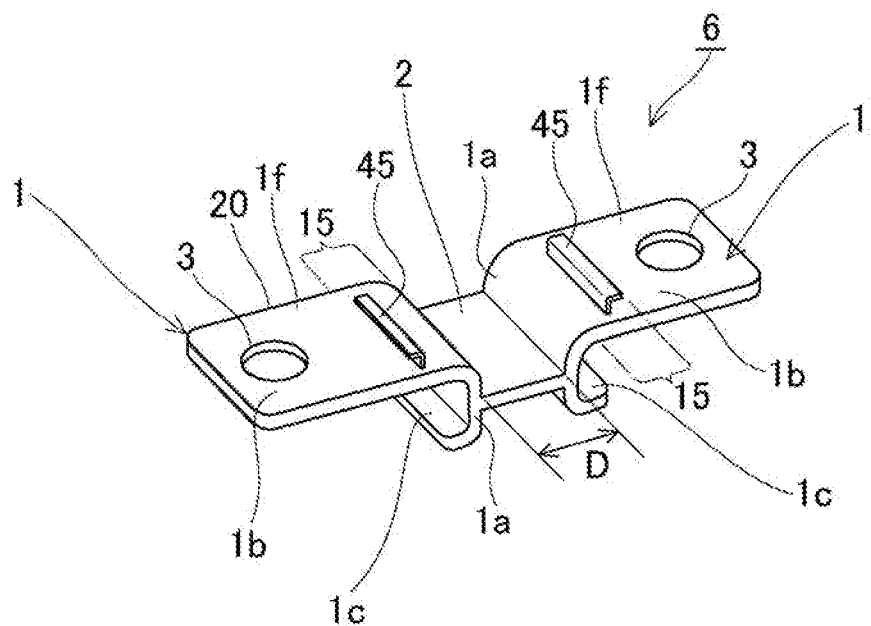
FIG. 12: A perspective view of the voice disorder treatment tool illustrated as the seventh embodiment of the present invention.

Next, a seventh embodiment of the present invention will be described with reference to FIG. 12. In the present embodiment, the description focuses on the differences from the third embodiment, and thus the same components as those of the third embodiment are denoted using the same reference numerals, and descriptions thereof will be omitted.

In the treatment tool 6 of the seventh embodiment, a handle section 45 is formed on a front surface 1*f* of the front surface piece 1*b*.

The handle section 45 protrudes from the front surface 1*f* of the front surface piece 1*b* and is bent in a tip end direction of the front surface piece 1*b*.

The handle section 45 is formed on both of the paired clamping sections 1, 1, and can easily and reliably be held using a jig (not illustrated). Thus, the effect of making it possible to improve the operability of the treatment tool 6 is achieved.

The treatment tool 6 including the handle sections 45 is particularly effective when holes are not formed in the bending region 15, and when the space between the holes 3 formed near the end surface sections 1*a* is large, making it difficult to grip the treatment tool 6 by a jig.

Figure 13:
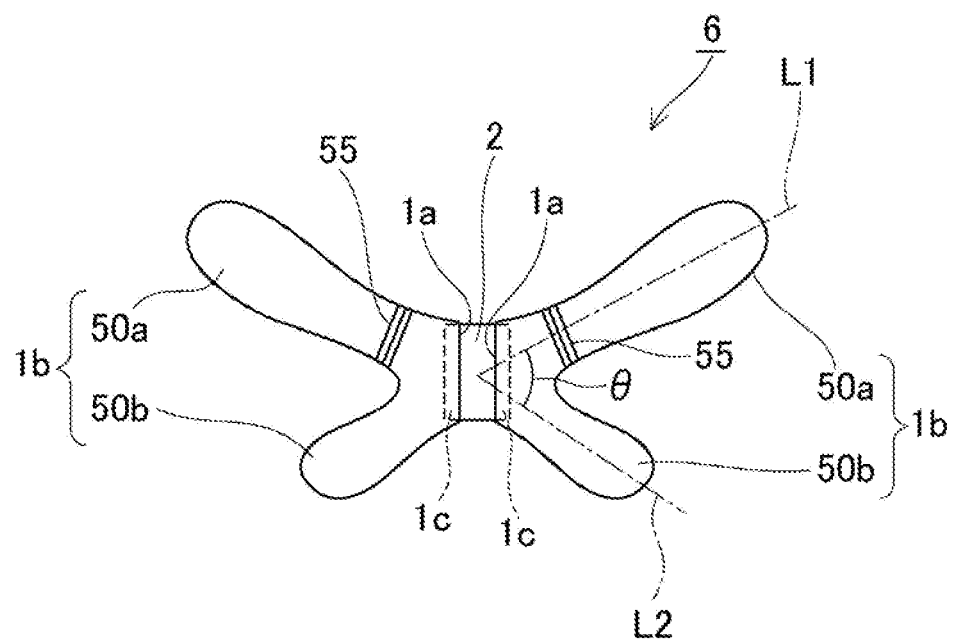
FIG. 13: A planar view of the voice disorder treatment tool illustrated as the eighth embodiment of the present invention.

Next, an eighth embodiment of the present invention will be described with reference to FIG. 13. In the present embodiment, the description focuses on the differences from each embodiment, and thus the same components as those of the above-described embodiments are denoted using the same reference numerals, and descriptions thereof will be omitted.

The treatment tool 6 of the eighth embodiment includes branched pieces 50*a*, 50*b* in which the front surface pieces 1*b* branch from the end surface sections 1*a* into two directions and come into contact with the front surfaces 11*a* of the cut ends 12 (refer to FIG. 3; hereinafter the same) of the thyroid cartilage 11.

The shapes of the branched pieces 50*a*, 50*b* toward the tip ends are rounded and formed into a bulbous oblong shape (slender racket shape).

The branched piece 50*a* is disposed obliquely upward with respect to the cut end 12. The branched piece 50*b* is disposed obliquely downward with respect to the cut end 12. The branched piece 50*a* is formed with a greater extending dimension than that of the branched piece 50*b*.

An angle θ formed by a center line L1 of the branched piece 50*a* and a center line L2 of the branched piece 50*b* is not particularly limited as long as less than 180 degrees.

The left and right branched pieces 50*a*, 50*b* are thus formed into a substantially X shape as a whole, in a planar view. Note that the configuration of the end surface section 1*a* and the rear surface piece 1*c* are the same as that in the first embodiment and the like.

The treatment tool 6 of the present embodiment can retain a suture thread 55 in the cut ends 12 while the suture thread 55 is wound at a base end section (that is, at or near the end surface section 1*a*) of the branched piece 50*a* or the branched piece 50*b* formed with a small width dimension.

The treatment tool 6 having the above configuration can thus be fixed to the cut ends 12 with the suture thread 55 without formation of the hole 3, achieving the effect of making the front surface piece 1*b* less susceptible to breakage.

Further, the branched pieces 50*a*, 50*b* are attached obliquely upward and obliquely downward with respect to the front surfaces 11*a* of the cut ends 12, and thus a bending angle aligned to the thyroid cartilage 11 can be made smaller. Thus, the effect of making the front surface piece 1*b* less susceptible to breakage is achieved.

Further, the effect of making the branched pieces 50*a*, 50*b* easy to attach in accordance with the shape of the cut ends 12 is achieved.

Further, because formation of the hole through which the suture thread is passed in the front surface piece 1*b* can be avoided, the treatment tool 6 achieves the effect of making it possible to increase the rigidity of the front surface piece 1*b* compared to a case where a hole is formed.

Further, because the treatment tool 6 can be fixed to the thyroid cartilage 11 without formation of a hole through which the suture thread passes in the front surface piece 1*b*, the effect of making it possible to prevent the concentration of stress caused by vibration during speech is achieved.

Note that the reinforcing structure S of an embodiment of the present invention may be configured by the clamping sections 1 formed by bending the front surface pieces 1*b* in advance in accordance with the shapes of the cut ends 12.

According to this configuration, it is possible to prevent metal fatigue that occurs particularly in the periphery of the bending region 15 by vibration during speech and deglutition, and suppress damage to the front surface piece 1*b*.

Further, the configuration in which the front surface piece 1*b* is bent to a certain extent in accordance with the shape of the cut end 12 may be applied to the treatment tool 6 of each of the above-described embodiments.

Further, the treatment tool 6 described in each of the above embodiments may be suitably combined to form a voice disorder treatment set that includes an upper and lower pair disposed above and below the cut ends 12.

The target voice disorder of the treatment tool 6 according to the embodiment of the present invention is particularly known as spasmodic dysphonia, a condition resulting in hoarseness caused by excessive glottic closure during speech, and voice loss while talking. Spasmodic dysphonia includes an adductor type in which the vocal cords excessively close when trying to speak, an abductor type in which the vocal cords excessively open when trying to speak, and a mixed type thereof. The present invention is preferably applicable to the adductor type, which accounts for the vast majority of cases. In other words, the treatment tool 6 of the present invention can be applied to the treatment of a condition in which, for some reason, excessive glottic closure is observed during speech, or the cause of the voice disorder is recognized as related to excessive glottic closure.

REFERENCE SIGNS LIST

1 Clamping section
1*a* End surface section
1*b* Front surface piece
1*c* Rear surface piece
1*d* Front surface contacting section
2 Bridging section
3 Hole
3 Opening end edge
6 Treatment tool (voice disorder treatment tool)
11 Thyroid cartilage
15 Bending region 12 Cut end
20 Side end edge
25 Projecting line
30 Notch
35 Recessed line
K Virtual line
S Reinforcing structure
x Longitudinal direction
y Width direction

The invention claimed is:

1. A voice disorder treatment tool comprising:
a plurality of clamping sections each of which comprises:
a front surface piece configured to be disposed on a front surface of incised thyroid cartilage; and
a rear surface piece configured to be disposed on a rear surface of the thyroid cartilage,
wherein the front piece and the rear surface piece are configured to fit to cut ends of the incised thyroid cartilage facing each other; and
a bridging section that connects the plurality of clamping sections,
wherein the front surface piece of the each of the clamping sections has a bending region deformable around a virtual line extending in a width direction of the front surface piece,
the bending region comprises at least one hole configured to allow a suture thread to be inserted therethrough, and
the at least one hole in the bending region is in a long hole shape extending in a direction that intersects in the width direction.

2. A voice disorder treatment tool comprising:
a plurality of clamping sections each of which comprises:
a front surface piece configured to be disposed on a front surface of incised thyroid cartilage; and
a rear surface piece configured to be disposed on a rear surface of the thyroid cartilage,
wherein the front piece and the rear surface piece are configured to fit to cut ends of the incised thyroid cartilage facing each other; and
a bridging section that connects the plurality of clamping sections,
wherein the front surface piece of the each of the clamping sections has a bending region deformable around a virtual line extending in a width direction of the front surface piece,
the bending region has a reinforcing structure, and
the reinforcing structure is formed by making a thickness of the bending region, in part or in whole, greater than a thickness of other sections.

3. A voice disorder treatment tool, comprising:
a plurality of clamping sections each of which comprises:
a front surface piece configured to be disposed on a front surface of incised thyroid cartilage; and
a rear surface piece configured to be disposed on a rear surface of the thyroid cartilage,
wherein the front piece and the rear surface piece are configured to fit to cut ends of the incised thyroid cartilage facing each other; and
a bridging section that connects the plurality of clamping sections,
wherein the front surface piece of the each of the clamping sections has a bending region deformable around a virtual line extending in a width direction of the front surface piece,
the bending region has a reinforcing structure, and
the reinforcing structure comprises a notch that is configured to allow hooking of a suture thread, the notch being provided on each side end edge of both ends of the front surface piece in the width direction.

4. A voice disorder treatment tool, comprising:
a plurality of clamping sections each of which comprises:
a front surface piece configured to be disposed on a front surface of incised thyroid cartilage; and
a rear surface piece configured to be disposed on a rear surface of the thyroid cartilage,
wherein the front piece and the rear surface piece are configured to fit to cut ends of the incised thyroid cartilage facing each other; and
a bridging section that connects the plurality of clamping sections,
wherein the front surface piece of the each of the clamping sections has a bending region deformable around a virtual line extending in a width direction of the front surface piece,
the bending region has a reinforcing structure, and
the reinforcing structure comprises a recessed line that is configured to allow hooking of a suture thread, the recessed line being provided on a front surface of the front surface piece.

5. A voice disorder treatment tool, comprising:
a plurality of clamping sections each of which comprises:
a front surface piece configured to be disposed on a front surface of incised thyroid cartilage; and
a rear surface piece configured to be disposed on a rear surface of the thyroid cartilage,
wherein the front piece and the rear surface piece are configured to fit to cut ends of the incised thyroid cartilage facing each other; and
a bridging section that connects the plurality of clamping sections,
wherein the front surface piece of the each of the clamping sections has a bending region deformable around a virtual line extending in a width direction of the front surface piece,
the bending region has a reinforcing structure, and
the front surface piece comprises a handle section that is configured to allow gripping by a tool.

6. A voice disorder treatment tool, comprising:
a plurality of clamping sections each of which comprises:
a front surface piece configured to be disposed on a front surface of incised thyroid cartilage; and
a rear surface piece configured to be disposed on a rear surface of the thyroid cartilage,
wherein the front piece and the rear surface piece are configured to fit to cut ends of the incised thyroid cartilage facing each other; and
a bridging section that connects the plurality of clamping sections,
wherein the front surface piece of the each of the clamping sections has a bending region deformable around a virtual line extending in a width direction of the front surface piece,
the bending region has a reinforcing structure, and
the front surface piece of at least one of the plurality of the clamping sections branches into two directions.

7. A voice disorder treatment tool, comprising:
a plurality of clamping sections each of which comprises:
a front surface piece configured to be disposed on a front surface of incised thyroid cartilage; and
a rear surface piece configured to be disposed on a rear surface of the thyroid cartilage,
wherein the front piece and the rear surface piece are configured to fit to cut ends of the incised thyroid cartilage facing each other; and a bridging section that connects the plurality of clamping sections, wherein the front surface piece of the each of the clamping sections has a bending region deformable around a virtual line extending in a width direction of the front surface piece, the bending region has a reinforcing structure, and the front surface piece is configured to curve along the incised thyroid cartilage in the bending region.

8. A voice disorder treatment set, comprising a plurality of the voice disorder treatment tools, wherein each of the plurality of the voice disorder treatment tools comprises:

a plurality of clamping sections each of which comprises:

a front surface piece configured to be disposed on a front surface of incised thyroid cartilage; and a rear surface piece configured to be disposed on a rear surface of the thyroid cartilage, wherein the front piece and the rear surface piece are configured to fit to cut ends of the incised thyroid cartilage facing each other; and a bridging section that connects the plurality of clamping sections, wherein the front surface piece of the each of the clamping sections has a bending region deformable around a virtual line extending in a width direction of the front surface piece, and the bending region has a reinforcing structure, and the plurality of the voice disorder treatment tools are configured to be arranged above and below the incised thyroid cartilage.

9. The voice disorder treatment tool according to claim 1, wherein the long hole shape is an elliptical shape, a substantially rectangular shape, a shape having long sides that are mutually parallel to each other and short sides that are semicircular.

\* \* \* \* \*